(12) United States Patent
Doi et al.

(10) Patent No.: US 6,931,948 B2
(45) Date of Patent: Aug. 23, 2005

(54) MULTIPLE PIPETTE AND METHOD OF USING THE SAME

(75) Inventors: Shigeru Doi, Kyoto (JP); Naoki Nokoshimatsu, Kyoto (JP); Hideki Nishimura, Kyoto (JP)

(73) Assignee: Arkray, Inc., Kyoto (JP)

( * ) Notice: Subject to any disclaimer, the term of this patent is extended or adjusted under 35 U.S.C. 154(b) by 168 days.

(21) Appl. No.: 10/240,814

(22) PCT Filed: Apr. 6, 2001

(86) PCT No.: PCT/JP01/03013

§ 371 (c)(1),
(2), (4) Date: Oct. 4, 2002

(87) PCT Pub. No.: WO01/76754

PCT Pub. Date: Oct. 18, 2001

(65) Prior Publication Data

US 2003/0047010 A1 Mar. 13, 2003

(30) Foreign Application Priority Data

Apr. 7, 2000  (JP) ..................... 2000-106132

(51) Int. Cl.[7] .............. G01N 1/38; G01N 1/14; B01L 3/02
(52) U.S. Cl. ............... 73/864.18; 73/864.17; 73/864.22
(58) Field of Search ............ 73/864.16–864.18, 73/863.32, 864.22; 436/179–180; 422/100, 925, 928

(56) References Cited

U.S. PATENT DOCUMENTS

| | | | | |
|---|---|---|---|---|
| 3,143,393 A | * | 8/1964 | De Seguin Des Hons ............................ 73/863.32 X |
| 3,954,014 A | | 5/1976 | Andrew, Jr. et al. | |
| 4,504,444 A | * | 3/1985 | Englander | .............. 422/100 |
| 4,523,484 A | * | 6/1985 | Kadota et al. | ....... 73/864.16 X |
| 5,330,721 A | * | 7/1994 | Tervamaki | .......... 422/928 X |
| 5,747,709 A | | 5/1998 | Oshikubo | |
| 5,820,824 A | * | 10/1998 | Tanaka | ............... 422/100 |
| 6,338,825 B1 | * | 1/2002 | Skeen | .................. 422/100 |

FOREIGN PATENT DOCUMENTS

| | | |
|---|---|---|
| DE | 43 21 062 | 1/1995 |
| EP | 0 475 517 | 3/1992 |
| JP | 2-13959 | 12/1984 |

* cited by examiner

Primary Examiner—Thomas P. Noland
(74) Attorney, Agent, or Firm—Hamre, Schumann, Mueller & Larson, P.C.

(57) ABSTRACT

A multiple pipette (X) comprising a first pipette (1) and a second pipette (2), wherein the first pipette (1) allows a liquid stored in a liquid storing section (17a) to be delivered a plurality of times by a fixed amount each and the second pipette (2) allows a liquid drawn in from outside to be delivered all at a time. The first pipette (1) is designed to deliver a liquid a plurality of times by a fixed amount each, e.g., by utilizing a ratchet mechanism (12d, 13a). The first pipette (1) preferably has a cap (19) removably attached to the front end thereof.

11 Claims, 4 Drawing Sheets

MULTIPLE PIPETTE AND METHOD OF USING THE SAME

TECHNICAL FIELD

The present invention relates to a multiple pipette having a plurality of pipettes and a method of using the same. Such multiple pipettes include ones for dispensing plural kinds of liquids separately and others for mixing plural kinds of liquids or diluting a target liquid for dispensing the mixed liquid or the diluted liquid.

BACKGROUND ART

For measuring the concentration of a particular component in a sample liquid, there exists a method in which the sample liquid containing an unknown concentration of the particular component and a reference liquid containing a known concentration of the particular component are bridged for measuring a potential difference generated therebetween to thereby compute the concentration of the particular component from the measured potential difference.

In this method, a concentration measuring plate is set, for example, to an analyzing apparatus for determining the concentration of the particular component.

The analyzing apparatus includes at least a set section for setting the plate, two probes, and computation means for computing the concentration of the particular component from the potential difference between the probes.

The plate includes at least a first liquid receiving portion to which a reference liquid is applied, a first terminal for conduction with the reference liquid applied to the first liquid receiving portion, a second liquid receiving portion to which a sample liquid is applied, a second terminal for conduction with the sample liquid applied to the second liquid receiving portion, and a bridge for shorting between the reference liquid in the first liquid receiving portion and the sample liquid in the second liquid receiving portion.

When the plate is set to the set section of the analyzing apparatus, the probes of the analyzing apparatus come into contact with the first terminal and the second terminal for measuring the potential difference between the reference liquid and the sample liquid. The computation means computes the concentration of the particular component of the sample liquid based on the measured potential difference.

A double pipette may be used for applying the reference liquid to the first liquid receiving portion and for applying the sample liquid to the second liquid receiving portion of the plate. For example, use maybe made of such a double pipette that includes a first pipette for drawing and dispensing the reference liquid through a liquid dispensing orifice and a second pipette for drawing and dispensing the sample liquid through a liquid dispensing orifice. The first pipette and the second pipette are held in a casing for example so that the distance between respective liquid dispensing orifices corresponds to the distance between the first liquid receiving portion and the second liquid receiving portion of the plate. The liquid dispensing orifice of each pipette may be an opening of a tip attached to the tip end of the pipette.

The double pipette may have the following problems when the reference liquid previously drawn in remains in the tip. Firstly, the amount of dispensing fluctuates when the remaining reference liquid is dispensed together with the reference liquid later drawn in. Such fluctuation of the dispensing amount also occurs when the first pipette cannot draw a liquid by a constant amount. Secondly, when the drawing and dispensing of a reference liquid is performed after a long interval from the previous drawing and dispensing of the reference liquid, the reference liquid remaining in the tip as adhered to the inner surface concentrates. The mixing of the concentrated liquid into the later sucked reference liquid causes the concentration of the reference liquid to vary.

When a sample liquid previously drawn in remains in the tip, the following problems may occur. Since the concentrations of a particular component may differ between the sample liquids to be measured, when the remaining sample liquid is mixed in a sample liquid to be measured next, the concentration of the sample liquid may vary.

Therefore, in the prior art double pipette, the tip of each pipette is replaced every time the reference liquid or the sample liquid is dispensed for avoiding the influence of the reference liquid or sample liquid previously drawn in and dispensed. However, this causes the following problems.

Firstly, since a large number of tips need be used, the pipette is disadvantageous in terms of the cost. The number of tips disposed of (as waste) is correspondingly large. Secondly, although the same reference liquid is used for plural measurements, the reference liquid need be drawn in each time of the measurements. Therefore, the drawing work is troublesome when a large number of sample liquids need be measured. Moreover, even when a tip is replaced every time of the drawing and dispensing of the liquid, the problem of the sucking amount fluctuation is not solved. Therefore, it is still impossible to dispense the liquid by a fixed amount.

DISCLOSURE OF THE INVENTION

According to a first aspect of the present invention, there is provided a multiple pipette which includes a first pipette for dispensing a liquid stored in a liquid storing section divisionally a plurality of times each by a constant amount, and a second pipette for dispensing a liquid drawn from the outside all at a time.

In a preferred embodiment, the first pipette includes a piston rod for pushing out the liquid from the liquid storing section, and a cylinder accommodating the piston rod at least partially. The piston rod is formed with a plurality of successive ratchet grooves, whereas the cylinder is provided with a pawl for engagement with the plurality of ratchet grooves. The cylinder is movable in a first direction together with the piston rod with the pawl engaged in the ratchet groove and is movable in a second direction opposite the first direction separately from the piston rod.

In a preferred embodiment, the piston rod is provided with an operation knob, which is movable for moving the piston rod separately from the cylinder. Moving the operation knob in the first direction causes a gas in the liquid storing section to be discharged, whereas moving the operation knob in the second direction causes a liquid to be drawn into the liquid storing section.

In a preferred embodiment, the first pipette incorporates a slide piece for supporting the pawl. The pawl is held on the slide piece when the piston rod is moved by the operation knob.

In a preferred embodiment, the first pipette includes a piston rod for pushing out the liquid from the liquid storing section, and a housing accommodating the piston rod. The liquid storing section is defined by a syringe having an inner space, and the syringe is threadedly attached to the housing.

In a preferred embodiment, the first pipette includes a nozzle connected to the liquid storing section. The nozzle includes a dispensing orifice for dispensing the liquid in the liquid storing section to the outside.

The first pipette may include a cap removably attached for covering the dispensing orifice. The nozzle may be protected by a reinforcing portion.

According to a second aspect of the present invention, there is provided a method of using a multiple pipette which comprises a first pipette for dispensing a first liquid stored in a liquid storing section divisionally a plurality of times each by a constant amount, and a second pipette for dispensing a second liquid drawn from the outside all at a time. The first liquid may be a reference liquid containing a known concentration of a particular component, whereas the second liquid may be a sample liquid containing an unknown concentration of a particular component.

According to a third aspect of the present invention, there is provided a multiple pipette which comprises a first pipette for dispensing a first liquid stored in a liquid storing section divisionally a plurality of times each by a constant amount, and a second pipette for dispensing a second liquid drawn from the outside all at a time. The first liquid may be mixed with the second liquid or the second liquid may be diluted with the first liquid.

BEST MODE FOR CARRYING OUT THE INVENTION

Figure 1:
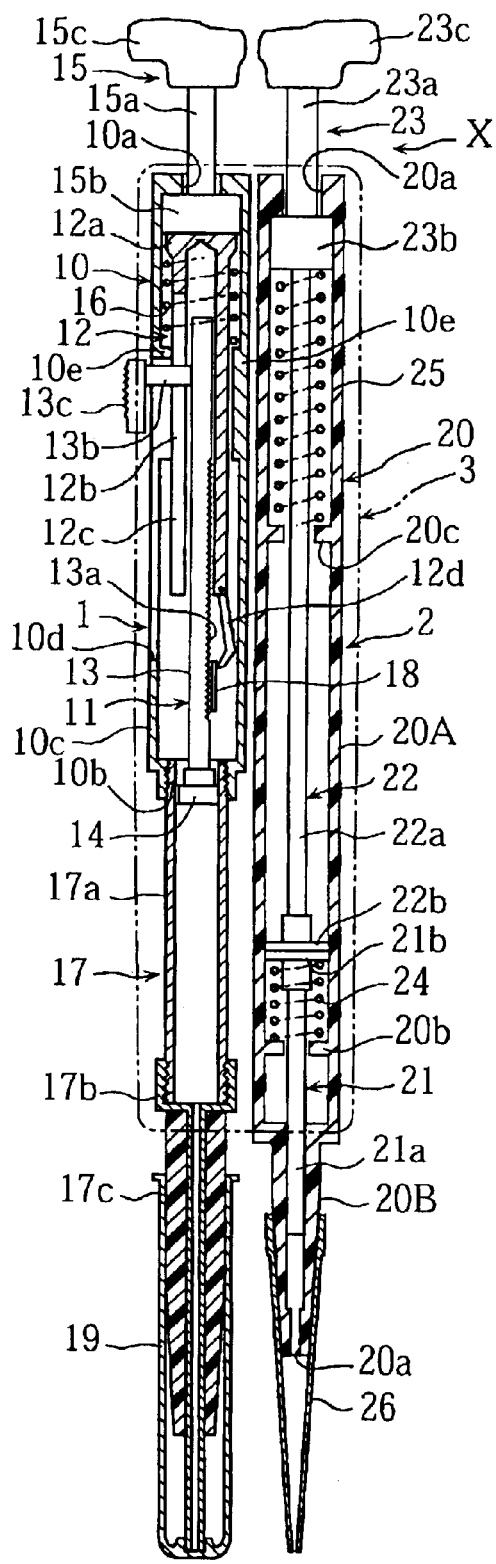
FIG. 1 is a sectional view illustrating an example of multiple pipette according to the present invention.

As shown in FIG. 1, a multiple pipette X includes a first pipette 1 and a second pipette 2. The first pipette 1 and the second pipette 2 are held in a casing 3.

The first pipette 1 includes a housing 10, a piston rod 11 and a cylinder 12. The piston rod 11 is held in the housing 1 with the upper end portion thereof received in the cylinder 12.

The piston rod 11 has a rod section 13 and a plug 14. The rod section 13 has an upper end portion to which an operation knob 13c is attached via an outwardly projecting pin 13b. As clearly shown in FIG. 2, the rod section 13 has a mid-portion formed with a plurality of successive ratchet grooves 13a.

As shown in FIG. 1, the cylinder 21 is formed, at the upper end portion thereof, with an engagement portion 12a which is larger in diameter than other portions. The cylinder 12 has a circumferential wall 12b formed with a slit 12c. The slit 12c extends longitudinally of the cylinder 12 for allowing the vertical movement of the pin 13b. The circumferential wall 12b has a lower end portion to which a pawl 12d is pivotally attached. As clearly shown in FIG. 2, the pawl 12d is in the form of a crank. The tip end of the pawl 12d is configured correspondingly to the configuration of the ratchet grooves 3a. Though not clearly shown in the figure, the pawl 12d is biased toward the piston rod 11 by a torsion coil spring for example. Therefore, when the pawl 12d moves downward, the pawl 12d engages the ratchet groove 13a, thereby moving the piston rod 11 downward together. On the other hand, when the pawl 12d moves upward, the pawl 12d does not engage the ratchet groove 13a so that the pawl 12d moves separately from the piston rod 11.

As shown in FIG. 1, the housing 10 has an upper opening 10a and a lower opening 10b.

A rod section 15a of a push rod 15 is inserted in the upper opening 10a. The push rod 15 has a plug 15b accommodated in the housing 10 in close contact with the upper surface of the cylinder 12. The rod section 15a has an upper end to which an operating portion 15c is attached. An engagement portion 10e is provided in the housing 10. A coil spring 16 is disposed between the engagement portion 10e and the engagement portion 12a of the cylinder 12. The coil spring 16 surrounds the upper end portion of the cylinder 12. Thus, the cylinder 12 and the push rod 15 are biased in the upward direction in FIG. 1.

A syringe 17 is threadedly fitted into the lower opening 10b of the housing 10. The syringe 17 includes a liquid storing section 17a to which a nozzle 17b is threadedly fitted. Thus, the syringe 17 is removable from the housing 10. The liquid storing section 17a is removable from the syringe 17. When removed, the liquid storing section 17a can be easily washed.

The nozzle 17b is in the form of a thin tube at portions except for the portion threadedly fitted to the liquid storing section 17a, so that a liquid retained in the liquid storing section 17a can be directly dispensed from the nozzle 17b. Therefore, the first pipette 1 does not require the use of tips. Therefore, the number of tips used by the multiple pipette can be reduced, which leads to reduction in cost and waste.

The tubular portion of the nozzle 17b is protected by a reinforcing portion 17c except for the tip end of the nozzle. A cap 19 for covering the tip end of the nozzle 17b is removably attached to the reinforcing portion 17c. Preferably, the cap 19 is attached so that the tip end of the nozzle 17c is held in close contact with the inner bottom surface of the cap.

The nozzle 17b is likely to be bent because of its thin tubular configuration. However, the provision of the reinforcing portion 17c prevents the nozzle 17b from being damaged. Further, the cap 19 can be easily attached owing to the provision of the reinforcing portion.

The attaching of the cap 19 to the nozzle 17b prevents the evaporation of the liquid retained in the liquid storing section 17a. Therefore, it is possible to prevent a particular component from concentrating due to the evaporation of water for example, so that the concentration of the liquid to be dispensed is kept unchanged for a long time.

Figure 2:
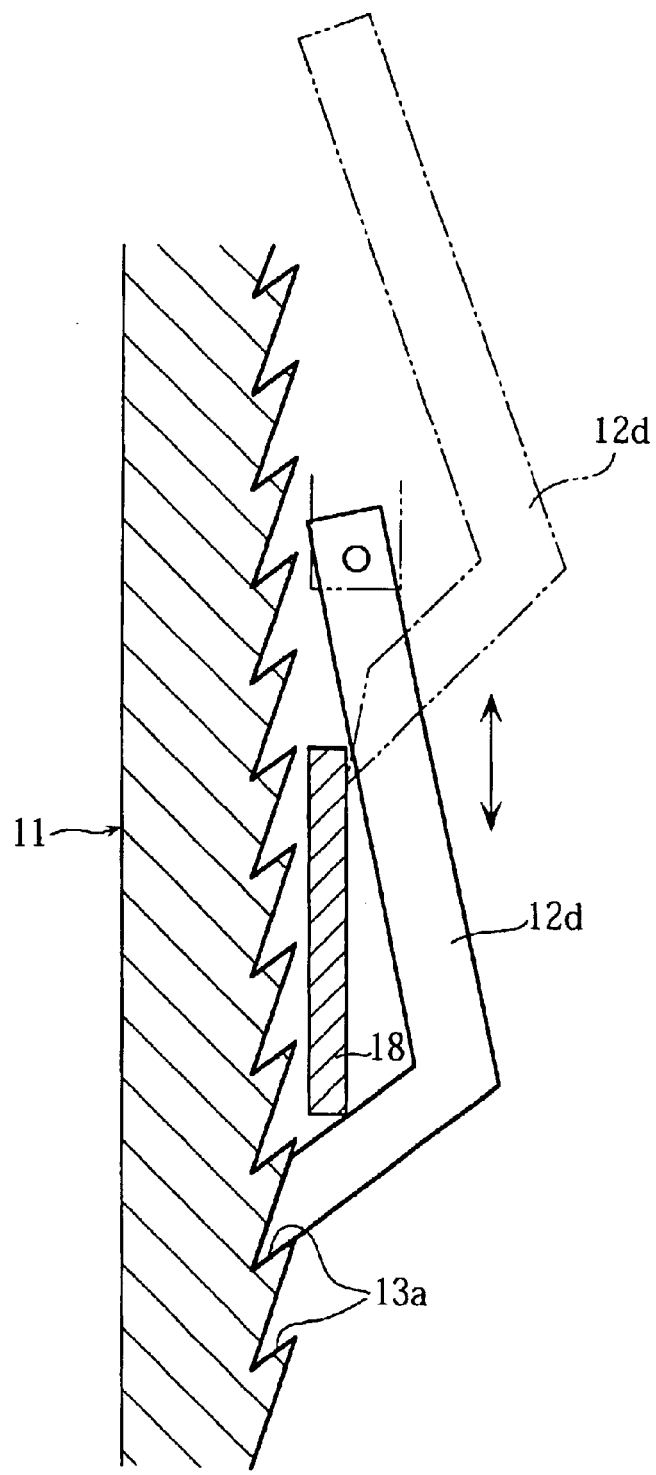
FIG. 2 is an enlarged view illustrating a principal part of the first pipette constituting the multiple pipette of FIG. 1.

As clearly shown in FIG. 2, a slide piece 18 is provided in the housing 10. The slide piece 18 is provided over the ratchet grooves 13a. In a normal state, the pawl 12d is held on the slide piece 18. While the pawl 12d moves downward for a distance corresponding to the width (the dimension in the vertical direction of FIG. 1) of the slide piece 18, the pawl 12d moves on the slide piece 18. When the pawl 12d moves downward for a distance exceeding the width of the slide piece, the pawl 12d drops from the slide piece 18 into engagement with the ratchet groove 13a. As described above, when the pawl 12d moves downward in the engaged state, the piston rod 11d moves downward together with the pawl 12d. When the pawl 12d moves upward, the pawl 12d moves as separated from the piston rod 11.

The housing 10 has a side wall 10c formed with a window 10d for allowing the vertical movement of the pin 13b. The plug 14 of the piston rod 11 is arranged in the liquid storing section 17b as closely fitted therein. Thus, when the pawl 12d is held on the slide piece 18, the vertical movement of the operation knob 13c makes the piston rod 11 move vertically within the housing 10 and the liquid storing section 17b.

In the first pipette 1, liquid is retained in the liquid storing section 17a in the following manner.

First, with the cap 19 removed, the operation knob 13c is moved downward to lower the piston rod 11, thereby discharging the gas from the liquid storing section 17a. Subsequently, with the operation knob 13c kept lowered, the tip end of the nozzle 17b is placed in liquid to be drawn. Then, the operation knob 13c is moved upward to raise the piston rod 11, thereby drawing the liquid into the liquid storing section 17a.

The liquid in the liquid storing section 17a is dispensed as follows. First, the operating portion 15c of the push rod 15 is moved downward to lower the cylinder 12 and the pawl 12d. As clearly shown in FIG. 2, since the pawl 12d is held on the slide piece 18 in the normal state, the pawl 12d moves downward on the slide piece 18 in accordance with the downward movement of the push rod 15. When the pawl 12d is further moved downward, the pawl 12d drops from the slide piece 18 into engagement with the ratchet groove 13a. When the push rod 15 is further lowered, the piston rod 11 moves downward together with the pawl 12d. As a result, the liquid in the liquid storing section 17a is pushed downward for dispensing from the tip end of the nozzle 17b by an amount in accordance with the amount of movement of the piston rod 11.

For dispensing a constant amount of liquid in each time of the operation, the stroke of the piston rod 11 in each time of the operation needs to be fixed. For this purpose, the stroke of the piston rod 11 is set equal to one pitch of the ratchet grooves 13a or to an integral multiple of one pitch. Accordingly, the stroke of the push rod 15 is the value obtained by adding the one pitch or an integral multiple of the one pitch of the ratchet grooves 13a to the movement distance of the pawl from the state held on the slide piece 18 until it comes into engagement with the ratchet groove 13a.

When the force applied to the operating portion 15c is released after the dispensing of liquid from the first pipette 1, the cylinder 12, the push rod 15 and the pawl 12d move upward due to the biasing force of the coil spring 16. At this time, the pawl 12d disengages from the ratchet groove 13a and moves upward again on the slide piece 18 to be held at its original position.

With the multiple pipette X, repeating of the operation of lowering the piston rod 11 by the exertion of a force to the operating portion 15c and then releasing the force enables repetitive dispensing of the liquid by a constant amount. Therefore, fluctuations of dispensing amount of liquid due to fluctuations of drawing amount of liquid can be avoided.

The second pipette 2 includes a housing 20, a piston rod 21 and an intermediate rod 22. The piston rod 21 and the intermediate rod 22 are accommodated in the housing 20.

The housing 20 includes a housing body 20A and a nozzle section 20B. The nozzle section is formed with a tip end opening 20a which provides communication between the inside and outside of the housing 20. The housing body 20A is formed, at the lower position and the middle position thereof, with engagement portions 20b, 20b projecting inwardly toward the center.

The piston rod 21 includes a rod section 21a and a plug 21. The plug 21 is accommodated in the housing body 20A. The rod section 21a is accommodated partially in the housing body 20A and partially in the nozzle section 20B. A coil spring 24 is disposed between the plug 21b and the engagement portion 20b of the housing body 20A. The coil spring 24 surrounds the upper end portion of the rod section 21a. The coil spring 24 biases the piston rod 21 in the upper direction in FIG. 1.

The intermediate rod 22 includes a rod section 22a and a plug 22b. The plug 22b is held in close contact with the plug 21b of the piston rod 21. Therefore, the intermediate rod 22 is also biased in the upper direction in FIG. 1.

The housing 22 has an upper surface formed with an opening 20a. A rod section 23a of a push rod 23 is inserted in the opening 20a. The push rod 23 is provided with a plug 23b, which is accommodated in the housing 20 as kept in close contact with the upper end of the intermediate rod 22. The rod section 23a has an upper end to which an operating portion 23c is attached. A coil spring 25 is disposed between the lower surface of the plug 23b and the engagement portion 20c of the housing body 20A. The coil spring 25 surrounds an upper portion of the intermediate rod 22. The coil spring 25 biases the pushing rod 23 upward.

With the second pipette 2, the drawing and dispensing of liquid is performed as follows.

First, a tip 26 is attached to the tip end of the nozzle section 20B. Subsequently, a force is exerted to the operating portion 23c of the push rod 23 to move the piston rod 21 and the intermediate rod 22 downward. Then, with the tip 26 placed in a sample liquid contained in a vial or a test tube, the force exerted to the push rod 23 is released. As a result, the piston rod 21, the intermediate rod 22 and the push rod 23 biased by the springs 24, 25 move upward to draw the liquid into the tip 26. For example, 20 μl of sample liquid is drawn.

The dispensing of the liquid is performed by moving the push rod 23 downward to push out the liquid from the tip 26. When the force applied to the push rod 23 is released, the push rod 23 returns to its original state due to the biasing force of the coil springs 24, 25.

The multiple pipette X is capable of dispensing two kinds of liquid. For example, a reference liquid containing a known concentration and a sample liquid containing an unknown concentration may be dispensed. Therefore, as shown in FIG. 4, the multiple pipette X may be used for simultaneously supplying a reference liquid and a sample liquid to a potential difference measuring plate 4 as shown in FIG. 3.

The potential difference measuring plate 4 is used for measuring a potential difference between a reference liquid and a sample liquid with an analyzing apparatus (not shown). In the analyzing apparatus, the concentration of a particular component of the sample liquid is computed in accordance with the measured potential difference.

Figure 3:
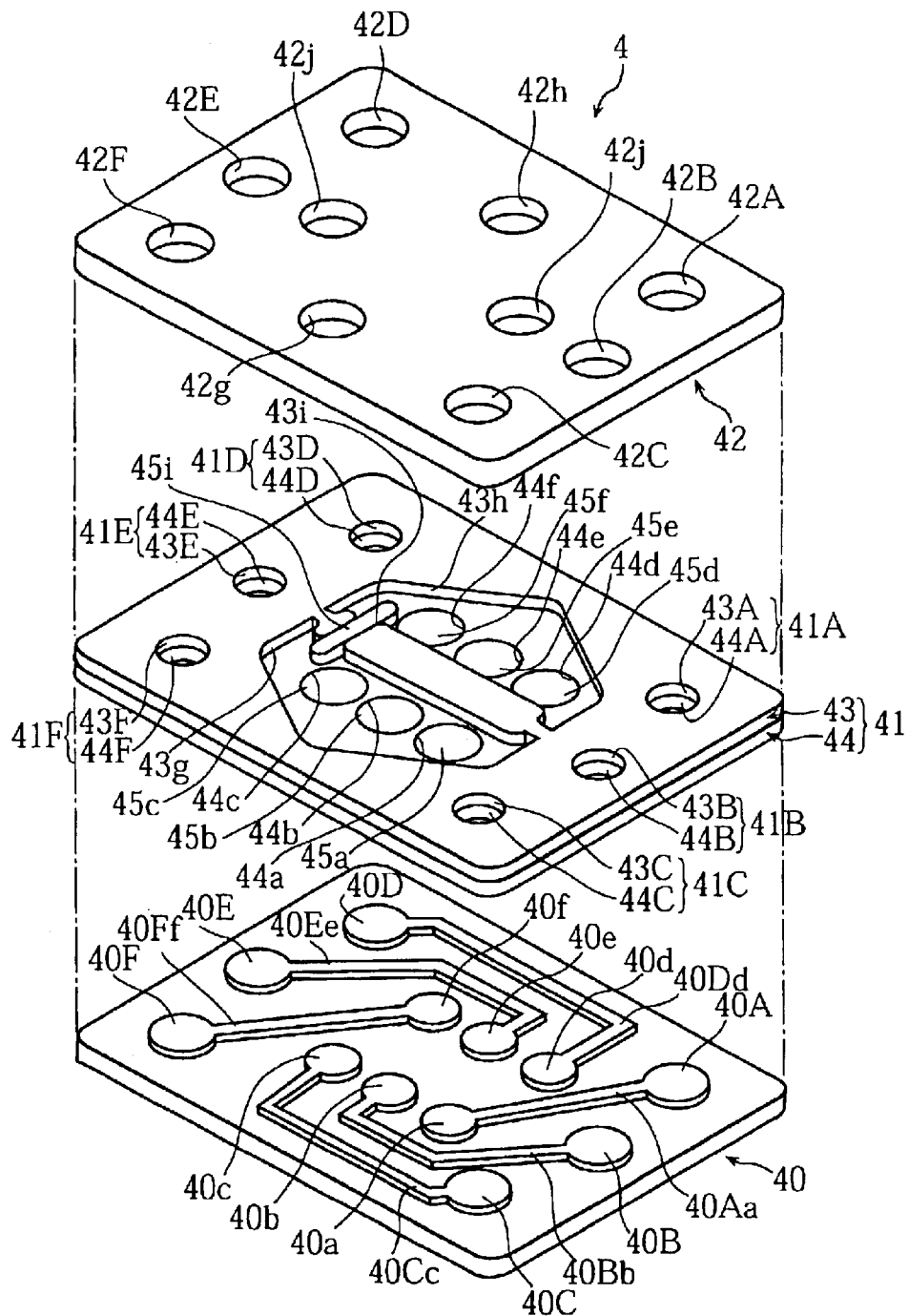
FIG. 3 is an exploded perspective view illustrating a potential difference measuring plate.
Figure 4:
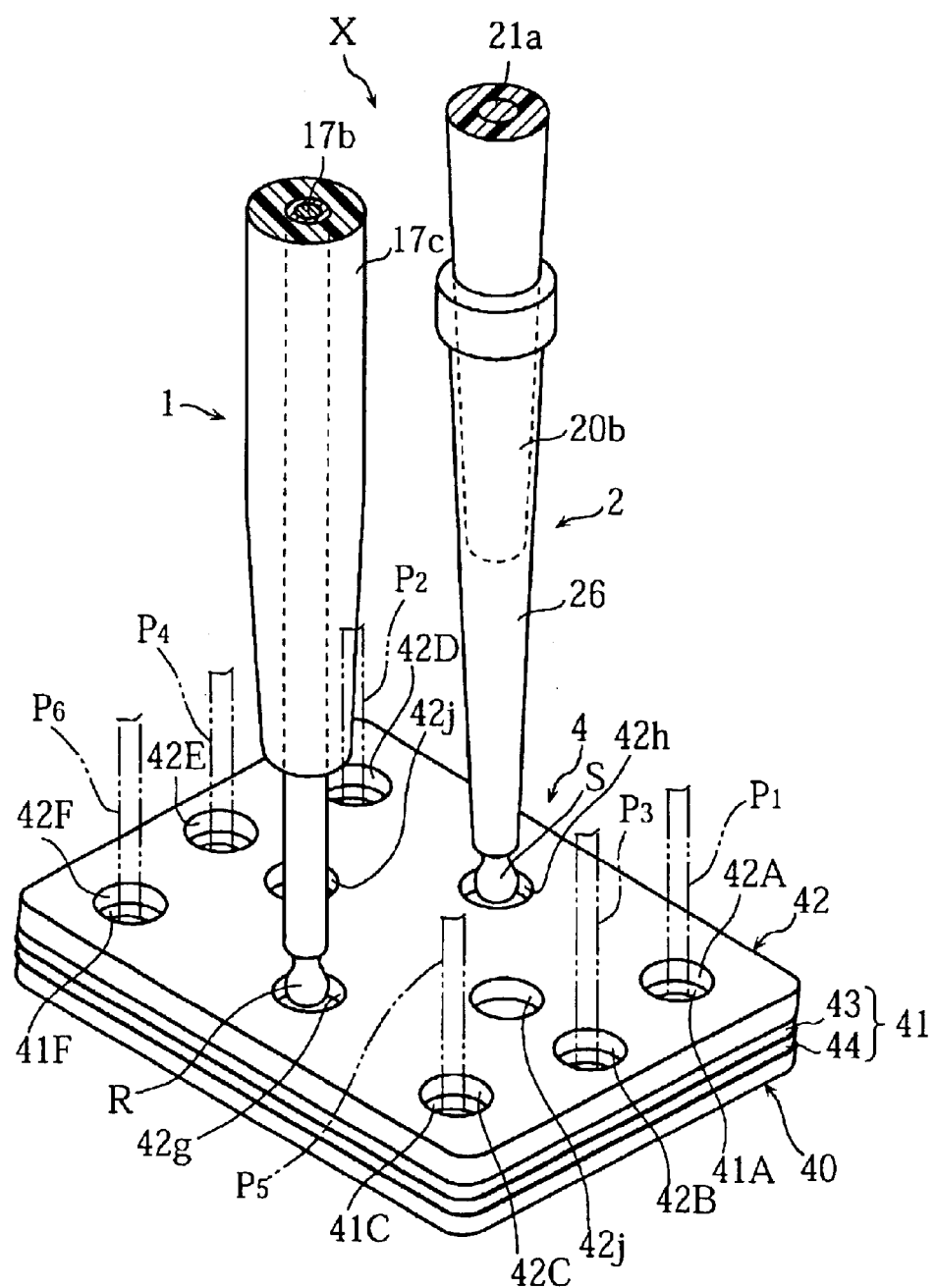
FIG. 4 is an enlarged view of a principal portion in a state where a reference liquid and a sample liquid are applied to the potential difference measuring plate of FIG. 3 using the multiple pipette of FIG. 1.

As clearly shown in FIG. 3, the potential difference measuring plate 4 includes a base film layer 40 on which a resist layer 41 and a cover film layer 42 are laminated. The potential difference measuring plate 4 measures the potential difference with respect to three kinds of ions such as $Na^+$, $Ka^+$ and $Cl^-$, for example.

The base film layer 40 has insulating properties. The base film layer 40 has an elongated rectangular configuration as a whole.

The base film layer 40 has an opposite pair of end edges respectively formed with three terminals 40A–40C and three terminals 40D–40F. The three terminals 40A–40C, 40D–40F are aligned widthwise of the base film layer 40. As will be described later, each of the terminals 40A–40F is brought into contact with a probe for measuring the potential difference.

The base film layer 40 is centrally formed with six liquid receiving pads 40a–40f. The liquid receiving pads 40a–40f are provided for receiving particular components of reference liquid or sample liquid. The liquid receiving pads 40a–40f are electrically connected to the terminals 40A–40F via conductive wires 40Aa, 40Bb, 40Cc, 40Dd, 40Ee and 40Ff, respectively.

The resist film layer 41 comprises a first resist film layer 43 and a second resist film layer 44. The first resist film layer 43 and the second resist film layer 44 have insulating properties. Each of the first resist film layer 43 and the second resist film layer 44 has an elongated rectangular configuration as a whole.

The resist film 41 has an opposite pair of end edges respectively formed with three insertion holes 41A–41C and three insertion holes 41D–41F. The insertion holes 41A–41F are provided at locations corresponding to the terminals 40A–40F of the base film layer 40. Each of the insertion holes 41A–41F is made up of a corresponding one of through-holes 43A–43F formed in the first resist film layer 43 and a corresponding one of through-holes 44A–44F formed in the second resist film layer 44. The terminals 40A–40F are exposed through the through-holes 41A–41F, respectively.

The second resist film layer 44 is centrally formed with six communication holes 44a–44f. The communication holes 44a–44f are respectively provided with ion selection membranes 45a–45f fitted therein. For example, the ion selection membranes 45a, 45d selectively pass $Na^+$, the ion selection membranes 45b, 45e selectively pass $K^+$, and the ion selection membranes 45c, 45f selectively pass $Cl^-$.

The first resist film 43 is centrally formed with a reference liquid retaining opening 43g and a sample liquid retaining opening 43h. The reference liquid retaining opening 43g communicates with the three communication holes 44a, 44b, 44c. The sample liquid retaining opening 43h communicates with the three communication holes 44d, 44e, 44f. The reference liquid retaining opening 43g communicates with the reference liquid retaining opening 43h through a cutout 43i. A bridge 45i for allowing the movement of ions is disposed in the cutout 43i.

The cover film layer 42 has an opposite pair of end edges respectively formed with three insertion holes 42A–42C and three insertion holes 42D–42F. The insertion holes 42A–42F communicate with the insertion holes 41A–41F of the resist film layer 41, respectively. Therefore, the terminals 40A–40F of the base film layer 40 are exposed through the relevant insertion holes 41A–41F.

The cover film layer 42 has an opposite pair of longitudinal edges which are centrally formed with a reference liquid receiving hole 42g and a sample liquid receiving hole 42h, respectively. The reference liquid receiving hole 42g communicates with the reference liquid retaining opening 43g of the first resist film layer 43. The sample liquid receiving hole 42h communicates with the sample liquid retaining opening 43h of the first resist film layer 43. The cover film layer 42 is further formed with insertion holes 42B, 42E and two air vents 42j provided adjacent to the insertion openings. Each of the air vents 42j communicates with both the reference liquid retaining opening 43g and the sample liquid retaining opening 43h.

For applying a reference liquid R and a sample liquid S to the potential difference measuring plate 4, the tip end of the nozzle 17b of the first pipette 1 is positioned at the reference liquid receiving hole 42g, whereas the tip end of the tip 26 attached to the second pipette 2 is positioned at the sample liquid receiving hole 42h. Then, respective operating portions 15c, 23c of the push rods 15, 23 of the pipettes 1, 2 are moved downward. As a result, a predetermined amount of reference liquid R is dispensed from the first pipette 1 and the reference liquid R is applied to the plate through the reference liquid receiving hole 42g. Form the second pipette 2, a predetermined amount of sample liquid S is dispensed and applied to the plate through the sample liquid receiving hole 42h.

The reference liquid applied through the reference liquid receiving hole 42g is retained in the reference liquid retaining opening 43g, whereas the sample liquid S applied through the sample liquid receiving hole 42h is retained in the sample liquid retaining opening 43h. Since the reference liquid retaining opening 43g is connected to the sample liquid receiving hole 42h via the cutout 43i provided with the bridge 45i, the reference liquid R and the sample liquid S are short-circuited.

The $Na^+$, $K^+$, $Cl^-$ ions in the reference liquid R retained in the reference liquid retaining opening 43g pass through the relevant ion selection membranes 45a, 45b, 45c to reach the reference liquid receiving pads 40a, 40b, 40c. The $Na^+$, $K^+$, $Cl^+$ ions in the sample liquid S retained in the sample liquid retaining opening 43h pass through the relevant ion selection membranes 45d, 45e, 45f to reach the sample liquid receiving pads 40d, 40e, 40f. As a result, potential differences are generated between the reference liquid receiving pads 40a, 40b, 40c and the sample liquid receiving pads 40d, 40e, 40f, respectively, due to the concentration difference of $Na^+$, $K^+$ or $Cl^-$ between the reference liquid R and the sample liquid S.

The potential differences are measured by potential difference measurement means (not shown) having six probes $P_1$–$P_6$. The potential difference due to the $Na^+$ concentration difference is measured by bringing probes $P_1$, $P_2$ into contact with the terminals 40A, 40D. The potential difference due to the $K^+$ concentration difference is measured by bringing probes $P_3$, $P_4$ into contact with the terminals 40B, 40E. The potential difference due to the $Cl^-$ concentration difference is measured by bringing probes $P_5$, $P_6$ into contact with the terminals 40C, 40F.

The concentration of each ion can be determined from the measured potential based on a calibration curve prepared in advance, for example.

With the multiple pipette X, the reference liquid R in the liquid storing section 17a can be dispensed as divided into a plurality of times each by a constant amount. Therefore, even in the case where the concentration measurement of a particular component is performed with respect to a plurality of sample liquids S, the drawing of the reference liquid R into the first pipette 1 need not be performed for each sample liquid R to be measured. The attachment and removal of the tip 26 relative to the first pipette 1 is also unnecessary. Therefore, the operation efficiency in applying the reference liquid R and the sample liquid S is enhanced. Since the first pipette 1 does not require tips, the total number of tips used by the multiple pipette X decreases, which leads to the reduction in cost and amount of the resulting waste.

In the multiple pipette according to the present invention, when the amount of liquid in the liquid storing section becomes insufficient, the liquid storing section may be replaced with another one containing sufficient reference liquid.

The multiple pipette according to the present invention may be used for mixing plural kinds of liquids or diluting a target liquid. In this case, respective liquid dispensing orifices of the first and the second pipettes may be made close to each other or combined with each other for mixing or diluting the liquids.

The multiple pipette according to the present invention may include three or more pipettes.

What is claimed is:

1. A multiple pipette comprising:

a first pipette for dispensing a first liquid stored in a liquid storing section divisionally a plurality of times each by a constant amount; and a second pipette for dispensing a second liquid drawn from outside all at a time;

wherein the first pipette includes a first housing, a first push rod for the divisional dispensing of the first liquid and an operating member for causing the first liquid to be drawn into the liquid storing section:

wherein the second pipette includes a second housing, and a second push rod for the dispensing of the second liquid;

wherein the first housing and the second housing are accommodated together in an overall casing;

wherein the first push rod and the operating member extend out beyond the first housing and the overall casing; and wherein the second push rod extends out beyond the second housing and the overall casing.

2. The multiple pipette according to claim 1, wherein the first pipette includes a piston rod for pushing our the liquid from the liquid storing section and a cylinder accommodating the piston rod at least partially and connected to the first push rod;

the piston rod being formed with a plurality of successive ratchet grooves;

the cylinder being provided with a pawl for engagement with the plurality of ratchet grooves;

the cylinder being movable in a first direction together with the piston rod with the pawl engaged in the ratchet groove and movable in a second direction opposite the first direction separately from the piston rod.

3. The multiple pipette according to claim 2, wherein the piston rod is connected to the operation member which is movable for moving the piston rod separately from the cylinder; and the operation member being moved in the first direction for causing a gas in the first liquid storing section to be discharged, the operation member being moved in the second direction for causing the first liquid to be drawn into the liquid storing section.

4. The multiple pipette according to claim 3, wherein the first pipette incorporates a slide piece for supporting the pawl, the pawl being held on the slide piece when the piston rod is moved by the operation member.

5. The multiple pipette according to claim 1, wherein the first pipette includes a piston rod accommodated in the first housing for pushing out the liquid from the liquid storing section;

the liquid storing section being defined by a syringe having an inner space, the syringe being threadedly attached to the first housing.

6. The multiple pipette according to claim 1, wherein the first pipette includes a nozzle connected to the liquid storing section, the nozzle including a dispensing orifice for dispensing the liquid from the liquid storing section to the outside.

7. The multiple pipette according to claim 6, wherein the first pipette includes a cap removably attached for covering the dispensing orifice.

8. The multiple pipette according to claim 6, wherein the nozzle is protected by a reinforcing portion.

9. A multiple pipette comprising:

a first pipette for dispensing a liquid stored in a liquid storing section divisionally a plurality of times each by a constant amount; and a second pipette for dispensing a liquid drawn front outside all at a time;

wherein the first pipette includes a piston rod for pushing out the liquid from the liquid storing section, and a cylinder accommodating the piston rod at least partially;

the piston rod being formed with a plurality of successive ratchet grooves;

the cylinder being provided with a pawl for engagement with the plurality of ratchet grooves;

the cylinder being movable in a first direction together with the piston rod with the pawl engaged in the ratchet groove and movable in a second direction opposite the first direction separately from the piston rod.

10. The multiple pipette according to claim 9, wherein the piston rod is provided with an operation knob which is movable for moving the piston rod separately from the cylinder; and the operation knob being moved in the first direction for causing a gas in the liquid storing section to be discharged, the operation knob being moved in the second direction for causing a liquid to be drawn into the liquid storing section.

11. The multiple pipette according to claim 10, wherein the first pipette incorporates a slide piece for supporting the pawl the pawl being held on the slide piece when the piston rod is moved by the operation knob.

* * * * *